United States Patent
Chang et al.

(10) Patent No.: US 9,931,239 B2
(45) Date of Patent: Apr. 3, 2018

(54) ASYMMETRIC MULTILAYER FILM FOR OSTOMY APPLICATION

(71) Applicant: HOLLISTER INCORPORATED, Libertyville, IL (US)

(72) Inventors: Moh-Ching Oliver Chang, Lake in the Hills, IL (US); Joel D. Shutt, Gurnee, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 69 days.

(21) Appl. No.: 14/204,474

(22) Filed: Mar. 11, 2014

(65) Prior Publication Data

US 2014/0221951 A1   Aug. 7, 2014

Related U.S. Application Data

(63) Continuation-in-part of application No. 13/837,867, filed on Mar. 15, 2013, now Pat. No. 9,050,387.

(60) Provisional application No. 61/761,981, filed on Feb. 7, 2013.

(51) Int. Cl.
*A61F 5/445* (2006.01)
*A61F 5/443* (2006.01)

(52) U.S. Cl.
CPC .............. *A61F 5/445* (2013.01); *A61F 5/443* (2013.01); *Y10T 428/2495* (2015.01)

(58) Field of Classification Search
USPC .......................................... 604/332
See application file for complete search history.

(56) References Cited

U.S. PATENT DOCUMENTS

| 4,855,335 | A |   | 8/1989 | Neperud |
| 5,290,842 | A | * | 3/1994 | Sasaki ................... C09J 7/0221 524/271 |
| 5,559,165 | A |   | 8/1996 | Paul |
| 5,567,489 | A |   | 10/1996 | Allen et al. |
| 5,663,228 | A | * | 9/1997 | Sasaki ................... C09J 7/0221 524/271 |

(Continued)

FOREIGN PATENT DOCUMENTS

| EP | 0787580 A1 | 6/1997 |
| JP | H04357957 A | 12/1992 |

(Continued)

OTHER PUBLICATIONS

LOTADER® 4720, Specification Sheet, Arkema Goup, p. 1, www.matweb.com, Jan. 14, 2016.*

(Continued)

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

An asymmetric multilayer film for an ostomy pouch includes a barrier layer including a first side and a second side. At least one layer is arranged on the first side of the barrier layer, and at least one layer arranged on the second side of the barrier layer, in which the combined thickness of the at least one layer arranged on the first side of the barrier layer is at least two times greater than the combined thickness of the at least one layer arranged on the second side of the barrier layer. The asymmetric multilayer film has a thickness of about 25 μm to about 50 μm.

6 Claims, 2 Drawing Sheets

(56) References Cited

U.S. PATENT DOCUMENTS

| | | | |
|---|---|---|---|
| 5,721,025 A * | 2/1998 | Falla | B32B 27/32 156/145 |
| 5,783,269 A | 7/1998 | Heilmann et al. | |
| 5,806,983 A | 9/1998 | Millon | |
| 5,846,620 A * | 12/1998 | Compton | B32B 27/08 428/34.6 |
| 5,856,387 A * | 1/1999 | Sasaki | C09J 7/0221 524/271 |
| 5,951,533 A | 8/1999 | Freeman | |
| 5,968,024 A | 10/1999 | Freeman | |
| 6,093,276 A | 7/2000 | Leise, Jr. et al. | |
| 6,258,423 B1 | 7/2001 | Giori | |
| 6,326,421 B1 | 12/2001 | Lipman | |
| 6,387,082 B1 | 5/2002 | Freeman | |
| 6,448,303 B1 | 9/2002 | Paul | |
| 6,451,883 B1 | 9/2002 | Chen et al. | |
| 6,451,912 B1 | 9/2002 | Kelch | |
| 6,455,161 B1 * | 9/2002 | Regnier | B32B 27/08 428/412 |
| 6,579,584 B1 * | 6/2003 | Compton | B29C 55/28 428/34.6 |
| 6,620,474 B1 | 9/2003 | Regnier et al. | |
| 6,628,474 B1 * | 9/2003 | Penman | G11B 17/04 360/137 |
| 6,685,683 B1 | 2/2004 | Clok et al. | |
| 6,770,342 B2 * | 8/2004 | Buongiorno | A61L 28/0026 428/36.6 |
| 6,946,182 B1 * | 9/2005 | Allgeuer et al. | 428/92 |
| 7,193,002 B2 | 3/2007 | Chen | |
| 7,217,853 B2 * | 5/2007 | Kulichikhin | A61L 15/585 106/205.01 |
| 7,255,903 B1 * | 8/2007 | Mudar | B65D 75/004 383/113 |
| 7,270,860 B2 | 9/2007 | Giori | |
| 7,344,568 B2 | 3/2008 | Chen | |
| 7,364,221 B2 * | 4/2008 | Tahri | C08J 9/06 181/295 |
| 7,442,739 B1 | 10/2008 | Hatfield | |
| 7,456,331 B2 * | 11/2008 | Kulichikhin | A61L 15/585 424/447 |
| 7,989,543 B2 * | 8/2011 | Karjala | C08F 210/16 524/543 |
| 2002/0002363 A1 * | 1/2002 | Urakawa | A61L 29/049 604/544 |
| 2002/0132071 A1 * | 9/2002 | Buongiorno | A61L 28/0026 428/35.2 |
| 2003/0225356 A1 * | 12/2003 | Kulichikhin | A61L 15/585 602/54 |
| 2004/0241246 A1 | 12/2004 | Lipman | |
| 2005/0080155 A1 | 4/2005 | Fattman et al. | |
| 2005/0273064 A1 * | 12/2005 | Dircks | B32B 7/12 604/322 |
| 2006/0034905 A1 | 2/2006 | Singh et al. | |
| 2006/0135924 A1 | 6/2006 | Luizzi | |
| 2006/0155025 A1 | 7/2006 | Arai et al. | |
| 2006/0199897 A1 * | 9/2006 | Karjala | A61L 15/58 524/543 |
| 2007/0051376 A1 * | 3/2007 | Kulichikhin | A61L 15/585 128/894 |
| 2007/0078197 A1 | 4/2007 | Samuelsen | |
| 2007/0215271 A1 * | 9/2007 | McClintic | B29C 63/02 156/247 |
| 2007/0237916 A1 | 10/2007 | Rasmussen et al. | |
| 2008/0161492 A1 * | 7/2008 | Cleary | A61K 9/7053 525/50 |
| 2008/0227886 A1 | 9/2008 | Cheney et al. | |
| 2008/0281037 A1 * | 11/2008 | Karjala | C08F 210/16 524/571 |
| 2009/0069764 A1 | 3/2009 | Burlot et al. | |
| 2009/0076186 A1 | 3/2009 | Lassalle | |
| 2009/0317614 A1 * | 12/2009 | Nilsen | B32B 27/32 428/219 |
| 2010/0028411 A1 | 2/2010 | Kawamura et al. | |
| 2010/0121290 A1 | 5/2010 | Rasmussen et al. | |
| 2010/0326598 A1 | 12/2010 | Atwater | |
| 2011/0118363 A1 * | 5/2011 | Jensen | A61L 15/30 514/772.4 |
| 2011/0130698 A1 | 6/2011 | Kutsukake et al. | |
| 2011/0162782 A1 | 6/2011 | Goubard | |
| 2011/0306677 A1 | 12/2011 | Kataoka | |
| 2012/0232504 A1 * | 9/2012 | Chang | A61F 5/445 604/332 |

FOREIGN PATENT DOCUMENTS

| | | |
|---|---|---|
| WO | 2007076864 A1 | 7/2007 |
| WO | 2008097443 A1 | 8/2008 |
| WO | 2011062829 A1 | 5/2011 |
| WO | 2011157278 A1 | 12/2011 |
| WO | 2012027884 A1 | 3/2012 |
| WO | 2013102009 A1 | 7/2013 |
| WO | 2014123573 A1 | 8/2014 |

OTHER PUBLICATIONS

International Preliminary Search on Patentability for PCT/US2013/051295 dated Oct. 1, 2013.

International Preliminary Search on Patentability for PCT/US2015/018453 dated Jun. 17, 2015.

International Preliminary Report on Patentability issued by the International Bureau of WIPO in connection with PCT/US2013/051295 dated Aug. 20, 2015.

\* cited by examiner

ASYMMETRIC MULTILAYER FILM FOR OSTOMY APPLICATION

CROSS-REFERENCE TO RELATED APPLICATION DATA

This application is a continuation-in-part of U.S. application Ser. No. 13/837,867, filed Mar. 15, 2013 entitled "Sound Absorbing Ostomy Pouch", which claims the benefit of and priority of Provisional U.S. Application No. 61/761,981, filed Feb. 7, 2013 entitled, "Sound Absorbing Ostomy Pouch", the contents of which are incorporated fully by reference herein.

BACKGROUND

The present disclosure relates to ostomy appliances, and more particularly to an ostomy pouch made using a sound absorbing laminate including a sound absorbing adhesive.

Ostomy appliances for collecting body waste, such as ostomy pouches, are used by patients who have had surgery such as a colostomy, ileostomy, or urostomy. When body waste is released from a stoma, flatus gas is often released together with the waste. The flatus gas passing through the stoma can cause a vibratory transient in body tissue, which is uncontrollable by the patient. Such release of the flatus gas from the stoma can accompany indiscreet noise, which can cause embarrassment to the patient.

Ostomy pouches comprising a quiet film to reduce noise produced by ostomy pouches, for example, plastic crackling sound made by the ostomy pouch when a user moves around, have been developed. Examples of such a quiet film include multilayer films disclosed in Giori, U.S. Pat. No. 7,270,860, which is assigned to the assignee of the present application and incorporated herein in its entirety by reference. However, these quiet films could be improved upon, to better insulate the flatus noise to prevent embarrassment.

Chang et al, PCT Application No. PCT/US12/71953, which is assigned to the assignee of the present application and incorporated herein in its entirety by reference, discloses sound absorbing films, sound absorbing nonwovens, laminates thereof, and ostomy pouches made using such sound absorbing materials.

Because of the inherent severe medical, social, and personal concerns related to the need for use of an ostomy appliance, improvements in ostomy appliances are desired. Any appreciable improvement in such ostomy appliances to provide greater discretion and privacy is of great importance in the quality of life of the increasing number of ostomy patients. The present disclosure provides improved ostomy appliances according to various embodiments to enhance sound insulating properties of such ostomy appliances.

BRIEF SUMMARY

An asymmetric multilayer film useful for making ostomy pouches is provided according to various embodiments. The asymmetric multilayer film has a thickness that is significantly less than that of the multilayer films used for known ostomy pouches. For example, the asymmetric multilayer film may have a thickness that is about 30-80% of the thickness of the prior art multilayer films, yet still can provide comparable or better film properties for ostomy pouches.

In one aspect, an asymmetric multilayer film for an ostomy pouch is provided. The asymmetric multilayer film includes a barrier layer including a first side and a second side. At least one layer is arranged on the first side of the barrier layer, and at least one layer is arranged on the second side of the barrier layer, in which the combined thickness of the at least one layer arranged on the first side of the barrier layer may be at least two times greater than the combined thickness of the at least one layer arranged on the second side of the barrier layer. The asymmetric multilayer film may have a thickness of about 25 µm to about 50 µm.

In one embodiment, the at least one layer arranged on the first side of the barrier layer may include a seal layer and a tie layer, and the at least one layer arranged on the second side of the barrier layer may include an outer layer. The at least one layer arranged on the first side of the barrier layer may have the combined thickness of about 20 µm to about 40 µm, and the at least one layer arranged on the second side of the barrier layer may have the combined thickness of about 2 µm to about 10 µm.

The asymmetric multilayer film may have a seal layer/inner layer/tie layer/barrier layer/outer layer construction. The seal layer may have a thickness of about 5 µm to about 30 µm. The inner layer may have a thickness of about 0 µm to about 25 µm. The tie layer may have a thickness of about 2 µm to about 8 µm. The barrier layer may have a thickness of about 2 µm to about 10 µm, and the outer layer may have a thickness of about 2 µm to about 10 µm. In one embodiment, the seal layer has a thickness of about 14 µm, the inner layer has a thickness of about 14 µm, the tie layer has a thickness of about 4 µm, the barrier layer has a thickness of about 4 µm, and the outer layer has a thickness of about 4 µm. In another embodiment, the seal layer has a thickness of about 13 µm, the inner layer has a thickness of about 9 µm, the tie layer has a thickness of about 3 µm, the barrier layer has a thickness of about 4 µm, and the outer layer has a thickness of about 3 µm.

The seal layer may be formed from a blend comprising ethylene vinyl acetate copolymer (EVA) and ethylene-propylene copolymer (EP copolymer). The inner layer may be formed from a blend comprising EP copolymer and polypropylene/ethylene-propylene rubber (PP-EP rubber). The tie layer may be formed from a maleated ethylene methyl acrylate copolymer (EMA-MAH). The barrier layer may be formed from a blend comprising an amorphous polyamide and a functionalized rubber compound. The outer layer may be formed from EMA-MAH.

In another aspect, an ostomy pouch including a first wall and a second wall, in which the first wall and the second wall may be sealed along their peripheral edges to define a cavity, is provided. At least one of the first wall and the second wall may be formed from the asymmetric multilayer film according to any of above disclosed embodiments.

In one embodiment, the ostomy pouch further includes a nonwoven layer adhesively attached to at least one of the first and second walls, in which an adhesive layer is arranged between an outer layer of the asymmetric multilayer film and the nonwoven layer. The adhesive layer may be formed from a sound absorbing adhesive including a vinyl-bon-rich triblock copolymer.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
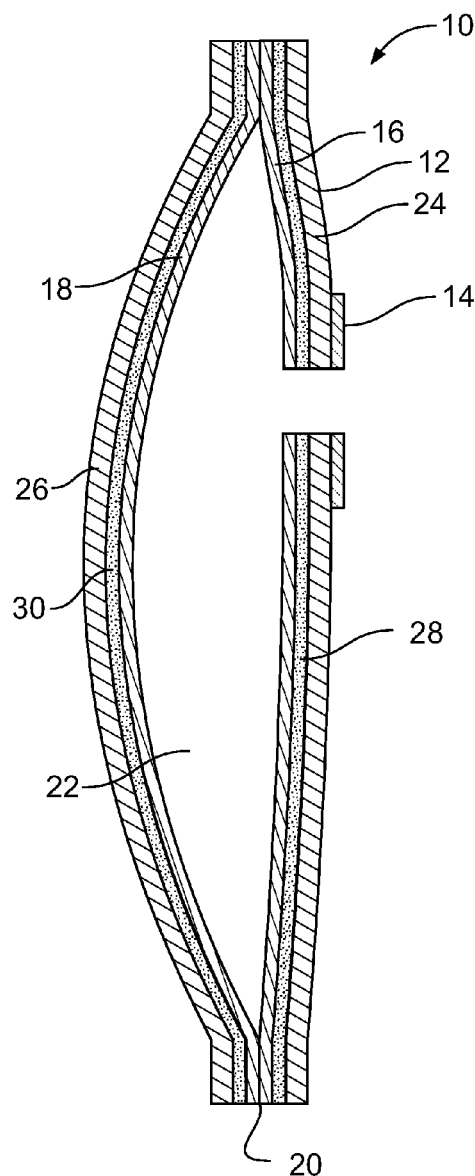
FIG. 1 is a cross-sectional illustration of an ostomy appliance including a pouch and a seal barrier in accordance with an embodiment of the present disclosure.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

FIG. 1 is a cross-sectional illustration of a one-piece ostomy appliance 10 according to an embodiment. The ostomy appliance generally includes a pouch 12 and a seal barrier 14. The pouch 12 includes first and second opposing walls 16, 18, which are sealed around peripheral edges 20 thereof by heat sealing or by any other suitable means to define a cavity 22 therebetween. The pouch 12 may also be formed from a tubular structure sealed around its open peripheral ends to define an interior chamber.

The pouch 12 also includes a first nonwoven layer 24 adhesively attached to the first wall 16 by a first adhesive 28 therebetween, and a second nonwoven layer 26 adhesively attached to the second wall 18 by a second adhesive 30 therebetween. Each of the first and second adhesive layers 28, 30 is formed of a sound absorbing adhesive including a vinyl-bond rich triblock copolymer.

The first and second walls 16, 18 are formed from a suitable polymeric film, and each of the walls can be formed from the same film or different films. The films can be a single layer film or a multilayer film, such as a multilayer film including an odor barrier layer used in commercially available ostomy pouches.

Preferably, each of the first and second walls 16, 18 is formed of a relatively thin multilayer film to allow for a thicker layer of the sound absorbing adhesive 28, 30. In one embodiment, the total thickness of a body side laminate including the first wall 16, the first sound absorbing adhesive 28 and the first nonwoven layer 24 is about 12.5 mil to about 16.5 mil, in which the first wall 16 is formed of a multilayer film having a thickness of about 1 mil to about 2 mil, the first sound absorbing adhesive has a thickness of about 0.5 mil to about 3.5 mil, and the first nonwoven layer has a thickness of about 11 mil. Similarly, the total thickness of an outer laminate including the second wall 18, the second sound absorbing adhesive 30, and the second nonwoven layer 26 is about 12.5 mil to about 16.5 mil, in which the second wall 18 is formed of a multilayer film having a thickness of about 1 mil to about 2 mil, the second sound absorbing adhesive has a thickness of about 0.5 mil to about 3.5 mil, and the second nonwoven layer has a thickness of about 11 mil.

Figure 2:
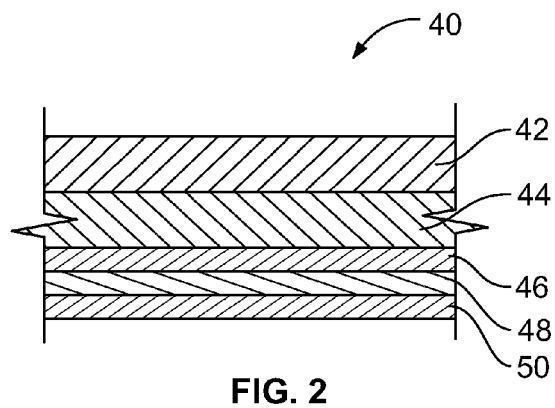
FIG. 2 is a cross-sectional illustration of a five-layer multilayer film for pouch walls according to an embodiment.

In this embodiment, each of the first and second walls 16, 18 is formed of a five-layer film having odor barrier properties and a thickness of about 25 µm to about 50 µm (about 1 mil to about 2 mil). FIG. 2 shows a cross sectional view of a five-layer film embodiment suitable for the first and second walls 16, 18. The five-layer film 40 includes a seal layer 42, an inner layer 44, a tie layer 46, a barrier layer 48, and an outer layer 50, and has a seal layer/inner layer/tie layer/barrier layer/outer layer construction.

The first and second walls 16, 18 may be formed from a multilayer film having an asymmetric film construction, in which more layers are provided on one side of a barrier layer than the other side of the barrier layer, and/or the combined thickness of the layers on one side of the barrier layer is thicker than that of the other side of the barrier layer, preferably at least two times thicker, and more preferably more than four times thicker, and still more preferably more than six times thicker. The asymmetric multilayer film may have a thickness of about 25 µm to about 50 µm, preferably about 30 µm to about 45 µm. One example of such an asymmetric multilayer film is the five-layer film 40 depicted in FIG. 2, in which three layers (i.e. the seal layer 42, the inner layer 44, and the tie layer 46) are provided on one side of the barrier layer 48, while only one layer (i.e. the outer layer 50) is provided on the other side of the barrier layer 48. The five-layer film 40 may also have an asymmetric thickness configuration, in which the combined thickness of the seal layer 42, the inner layer 44, and the tie layer 48 on one side of the barrier layer 48 is at least two times thicker than the outer layer 50 on the other side of the barrier layer 48.

The multilayer film 40 may include a seal layer 42 having a thickness of about 5 µm to about 30 µm, an inner layer 44 having a thickness of about 0 µm to about 25 µm, a tie layer 46 having a thickness of about 2 µm to about 8 µm, a barrier layer 48 having a thickness of about 2 ∞m to about 10 µm, and an outer layer 50 having a thickness of about 2 µm to about 10 µm. In one embodiment, the film 40 is an asymmetric five-layer film having a total thickness of about 40 µm and including a seal layer 42 having a thickness of about 14 µm, an inner layer 44 having a thickness of about 14 µm, a tie layer 46 having a thickness of about 4 µm, a barrier layer 48 having a thickness of about 4 µm, and an outer layer 50 having a thickness of about 4 µm. In another embodiment, the film 40 is an asymmetric five-layer film having a total thickness of about 32 µm and including a seal layer 42 having a thickness of about 13 µm, an inner layer 44 having a thickness of about 9 µm, a tie layer 46 having a thickness of about 3 µm, a barrier layer 48 having a thickness of about 4 µm, and an outer layer 50 having a thickness of about 3 µm. In yet another embodiment, the film 40 is an asymmetric five-layer film having a thickness of about 40 µm and including a seal layer 42 having a thickness of about 20 µm, an inner layer 44 having a thickness of about 8 µm, a tie layer 46 having a thickness of about 4 µm, a barrier layer 48 having a thickness of about 4 µm, and an outer layer 50 having a thickness of about 4 µm.

The seal layer 42 may be formed of a material having suitable heat sealability, such that the seal layers can be heat sealed to form a pouch. Suitable materials for the seal layer 42 include ethylene based polymers, such as copolymers of ethylene with vinyl esters, e.g. EVA and EMA, ethylene alpha olefin copolymers (ethylene based plastomers), ethylene based elastomers (olefin block copolymers, OBC), and ethylene-propylene (EP) copolymers (PP-elastomer), and blends thereof. Suitable EVA copolymers include those containing about 5 percent by weight (wt. %) to 35 wt. % vinyl acetate and more preferably, about 18 percent vinyl acetate, by weight of the copolymer. One exemplary material is available from ExxonMobil as product Escorene® Ultra FL00218. Such a material has a melting point temperature of 86° C. and a Shore A hardness of about 91. EVA is known to exhibit the necessary characteristics for joining to another EVA member, as by heat sealing, to provide an air-tight, liquid-tight seal at the joint or seal. EVA materials can be blended to facilitate formation and film extrusion. For example, an EVA blend can have about 98 wt. % EVA with about 2 wt. % anti-block and slip additives, in an EVA carrier. One suitable additive is available from A. Schulman Inc., as Polybatch® SAB-1982VA.

Suitable EMA copolymers can include about 5 wt. % to about 35 wt. % of the methyl acrylate and preferably about 15 wt. % to about 30 wt. % methyl acrylate. One such EMA copolymer is Lotryl® 18AM02 supplied by Arkema Inc. This copolymer has a melting point of about 83° C. and specific gravity of about 0.841. The EMA resins can also be blended with anti-block and slip additives in an EVA carrier. One suitable material for blending is the aforementioned Polybatch® SAB-1982VA. Such a blend can have, for example EMA at about 98 wt. %, with about 2 wt. % Polybatch® SAB-1982VA anti-block and slip additive.

Another suitable material is ethylene alpha olefin copolymers (ethylene based plastomers). An example of suitable ethylene alpha olefin copolymers is Exact® 0203 resin, supplied by ExxonMobil Corporation, which has a specific gravity of about 0.88, a Shore A hardness of about 95, a melting point temperature of about 95° C., and specific gravity of about 0.902. This resin is designed for both monolayer and multilayer co-extruded cast film applications and is suitable in applications that require toughness and heat sealing performance. Typical applications include film for industrial packaging.

Still another suitable material is ethylene based elastomers (olefin block copolymers, OBC), for example, Infuse® 9107 supplied by Dow. This material has a specific gravity of about 0.866, a Shore A hardness of about 60 and a melting point of about 121° C.

Still another suitable material is an ethylene-propylene copolymer (PP-elastomer) resin. It has a low modulus and thus exhibits low noise characteristics. It has excellent compatibility with polypropylene (PP) and polyethylene (PE). Preferably, ethylene-propylene copolymers include about 6 wt. % to about 18 wt. % ethylene. An example of suitable ethylene-propylene copolymers is Versify®2200 available from Dow Chemical. This resin is a PP-elastomer including about 9 wt. % ethylene and has melting point of about 82° C., a Shore A hardness of about 94 and a Shore D hardness of about 42. It has a specific gravity of about 0.878. Another example is Vistamaxx® 3980FL from Exxon, which is a PP-elastomer including about 8.5 wt. % ethylene.

Polymer blends comprising EVA, EMA, ethylene alpha olefin copolymers (ethylene based plastomers), ethylene based elastomers (olefin block copolymers, OBC), and ethylene-propylene (EP) copolymers (PP-elastomer) are also suitable for the seal layer. Examples include, but are not limited to, a blend of EVA copolymer (Escorene®FL00218 present at 49 wt. %) and ethylene-propylene copolymer (PP-elastomer, Versify®2200 present at 49 wt. %) with anti-block and slip additives, and a blend of EMA (Elvaloy®1330AC present at 49 wt. %) and PP-elastomer (Versify®2200 present at 49 wt. %) also with anti-block and slip additives. Blends of various EP copolymer resins are also suitable, for example, blends of Versify®2200 and Versify®3400, which is a similar EP copolymer resin, but has a higher melting point of about 97° C., a Shore A hardness of 72 and a Shore D hardness of 22, and a specific gravity of about 0.865. Suitable blends can have ratios of about 50 wt. % of Versify®2200 to about 75 wt. % of Versify®2200 of the blend. PP-elastomers such as Versify®, Vistamaxx®, and Notio® from Mitsui, and PP-EP rubber such as Adflex® Q100F from LyondellBasell are also suitable.

In one embodiment, the seal layer 42 may be formed from a blend including about 49 wt. % EVA (e.g. Escorene® Ultra FL00218), about 49 wt. % EP copolymer (e.g. Vistamaxx® 3980FL), and about 2 wt. % anti-block and slip additive (e.g. Polybatch® SAB-1982VA.)

In addition to heat sealability, the seal layers 42 can also provide sound absorbing properties to the film 40. In such an embodiment, the seal layer 42 comprises a vinyl-bond rich triblock copolymer, such as Hybrar® from Kuraray Co. Ltd. to enhance mechanical properties and sound absorbing properties of the film 40. For example, the seal layer 42 can be formed from a blend of a vinyl-bond rich styrene-isoprene-styrene (SIS) block copolymer (Hybrar® 5127), a PP-elastomer (Vistamaxx®), and an EMA (Lotryl® 20MA08).

The inner layer 44 is arranged adjacent the seal layer 42, and can impart mechanical (tear) strength to the film 40. The suitable seal layer materials are also suitable for the inner layer. For example, ethylene based polymers, such as copolymers of ethylene with vinyl esters, e.g. EVA and EMA, ethylene alpha olefin copolymers (ethylene based plastomers), ethylene based elastomers (olefin block copolymers, OBC), and ethylene-propylene (EP) copolymers (PP-elastomer), and blends thereof are suitable film forming materials for the inner layer.

In one embodiment, the inner layer 44 may be formed from a blend including about 65 wt. % EP copolymer (e.g. Vistamaxx® 3980FL) and about 35 wt. % PP-EP rubber (e.g. Adflex® Q100F.)

In some embodiments, the inner layer 44 can also provide sound absorbing properties. In such an embodiment, the inner layer 44 comprises a vinyl-bond rich triblock copolymer, such as Hybrar® to enhance mechanical properties and sound absorbing properties of the film 40. For example, the inner layer 44 can be formed from a blend of a vinyl-bond rich styrene-ethylene-propylene-styrene (SEPS) block copolymer (e.g. Hybrar® 7125) and a PP-elastomer (Vistamaxx®).

The tie layer 46 is arranged between the inner layer 44 and the barrier layer 48. The tie layer 46 facilitates adhesion of the barrier layer 48 to the remainder of the film structure. Suitable materials for the tie layer 46 include maleated polyolefins, such as a maleated ethylene methyl acrylate copolymers (EMA-MAH) having maleic anhydride present at about 0.3 wt. % and methyl acrylate present at about 20 wt. % of the resin. One such material is available from Arkema, Inc. as Lotader®4503. In one embodiment, the tie layer 46 is formed from a blend comprising 80 wt. % EMA (Lotryl® 18MA02 from Arkema, Inc.) and 20 wt. % maleated compound (Bynel®CXA41E710 from DuPont.)

In some embodiments, the tie layer 46 can also provide sound absorbing properties. In such an embodiment, the tie layer 46 comprises a vinyl-bond rich triblock copolymer, such as Hybrar® to enhance mechanical properties and sound absorbing properties of the film 40. For example, the tie layer 46 can be formed from a blend of a vinyl-bond rich SEPS block copolymer (e.g. Hybrar® 7125) and a maleated compound (such as Bynel®CXA41E710).

The barrier layer 48 can be formed of a suitable film having gas barrier properties, such as, but not limited to, polyvinylidene chloride, vinylidene copolymer, polyamide, and ethylene-vinyl alcohol copolymer. Preferably, the barrier layer 48 is formed from a non-chlorine containing polymer that is substantially impermeable to malodor causing compounds typically encountered in ostomy pouches. Such malodor causing compounds can include sulfur containing compounds and indoles. Suitable barrier layer materials include resins such as amorphous polyamide (nylon)

resin, which can be modified by an anhydride-modified olefinic polymer or copolymer, or an epoxy modified olefin polymer or copolymer to decrease the rigidity of the barrier layer. In one embodiment, the barrier layer 48 is formed from a blend of an amorphous polyamide, such as Selar® PA3426R from DuPont, and a functionalized rubber blend or compound, such as Lotader® 4720 from Arkema, Inc.

The outer layer 50 is arranged adjacent the barrier layer, and may facilitate adhesion of the film 40 to the sound absorbing adhesive layers 28, 30. The suitable tie layer materials are also suitable for the outer layer 50. For example, maleated ethylene methyl acrylate copolymers (EMA) having maleic anhydride present at about 0.3 wt. % and methyl acrylate present at about 20 wt. % of the resin (Lotader®4503) can be used to form the outer layer 50.

Figure 4:
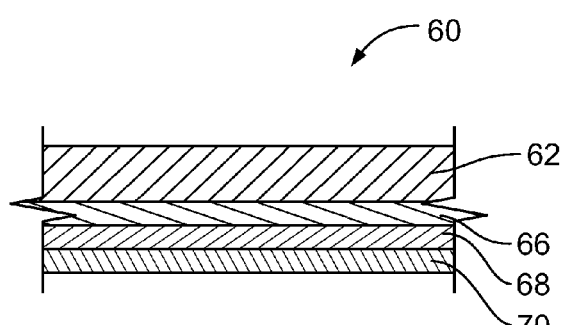
FIG. 4 is a cross-sectional illustration of a four-layer multilayer film according to an embodiment.

An asymmetric multilayer film suitable for the first and second walls 16, 18 may include less than five layers or more than five layers. For example, an asymmetric multilayer film 60 may include four layers having a seal layer 62/tie layer 66/barrier layer 68/outer layer 70 construction, as shown in FIG. 4. The asymmetric multilayer films can be used to make an ostomy pouch with a sound absorbing adhesive and a nonwoven layer according to various embodiments describes herein. However, the use of the asymmetric multilayer films is not limited to such applications, and the asymmetric multilayer films may also be used to form walls of various other ostomy pouches. For example, the asymmetric multilayer films may be used with a conventional adhesive and a non-woven layer to make ostomy pouches or may be directly sealed to a non-woven layer without an adhesive layer therebetween.

Other multilayer films with odor barrier properties having more than five layers or less than five layers can also be used to form one or both of the first and second walls 16, 18. For example, a seven-layer film having a structure ABCDCBA, where A represents seal layers, B represents inner layers, C represents tie layers, and D represents a barrier layer, can be used to form the first wall 16 and/or the second wall 18. A six-layer film including a barrier layer, two tie layers, an inner layer, and two seal layers (e.g. ABCDCA) can also be used to form the first wall 16 and/or the second wall 18. The walls 16, 18 can be formed of the same multilayer film or different multilayer films. In a preferred embodiment, the multilayer films for the first and second walls 16, 18 include at least one layer comprising a vinyl-bond rich triblock copolymer, such as vinyl-bond rich SIS block copolymer, e.g. Hybrar® 5125 and 5127, or vinyl-bond rich SEPS block copolymer, e.g. Hybrar® 7125, or vinyl-bond rich styrene-ethylene-ethylene-propylene-styrene (SEEPS) block copolymer, e.g. Hybrar® 7311.

Referring back to FIG. 1, the first and second walls 16, 18 are provided with the first and second nonwoven layers 24, 26, respectively, which are attached via the first and second adhesive layers 28, 30, respectively. In this embodiment, each of the first and second adhesive layers 28, 30 is formed of a sound absorbing adhesive comprising a vinyl-bond rich triblock copolymer. Suitable sound absorbing adhesives have high sound absorbing properties, good process coatability, and softness. In preferred embodiments, the sound absorbing adhesive formulation includes about 2 wt. %-about 50 wt. % vinyl-bond rich triblock copolymer, about 45 wt. %-about 85 wt. % tackifier, about 0 wt. %-about 30 wt. % end block modifying resin, about 0 wt. %-about 30 wt. % diluent, and about 0 wt. %-about 3 wt. % antioxidant, and has a tan delta at 25° C. of greater than about 1 between 150 Hz and 2,000 Hz frequencies, a viscosity of less than about 8,000 CP at 165° C., and G' of less than about 120,000 Pa at 25° C.

Suitable vinyl-bond rich triblock copolymers include vinyl-bond rich SIS block copolymers, such as Hybrar® 5125 and 5127, and vinyl-bond rich SEPS or SEEPS block copolymer, such as Hybrar® 7125 and 7311, respectively. Suitable elastomers include diblock copolymers, such as a diblock copolymer based on styrene and ethylene/propylene with a polystyrene content of about 28 wt. % (e.g., Kraton®G1702 from Kraton Polymers), polyisobutylene, polyisoprene, and styrene/butadiene copolymers. Suitable tackifiers include cycloaliphatic hydrocarbon (e.g., Escorez® from Exxon Chemical) and hydrocarbon resins (e.g., Regalite® from Eastman Chemical Company, Wingtack® from Goodyear Chemical). Suitable end block modifying resins include aromatic resins based on mixed C9 petroleum distillation streams, resins based on pure or mixed monomer streams of aromatic monomers such as homo or copolymers of vinyl toluene, styrene, alpha-methyl styrene (e.g., Kristalex® from Eastman Chemical Company), coumarone, and indene. Suitable diluents include polyisoprene and polybutenes (e.g., Indopol® from BP). Suitable antioxidants include typical antioxidants used in rubber based pressure sensitive adhesives, such as high molecular weight hindered phenols and multifunctional phenols such as sulfur and phosphorous-containing phenols.

In some embodiments, the sound absorbing adhesive is formulated including about 5 wt. % to 40 wt. % of a vinyl-bond rich SIS block copolymer, such as Hybrar® 5125 and 5127, about 7 wt. % to 23 wt. % of a cycloaliphatic hydrocarbon resin, such as Escorez® 5400, about 57 wt. % to 73 wt. % of liquid tackifying hydrocarbon resin, such as Wingtack®10, and about 11 wt. % to about 16 wt. %) of an end block modifying resin, such as Kristalex® 3085.

The sound absorbing adhesive may also be formulated including a vinyl-bond rich SIS block copolymer. For example, a sound absorbing adhesive can be formulated including about 5 wt. % to 40 wt. % of a vinyl-bond rich SEPS or SEEPS block copolymer, such as Hybrar® 7125 and 7311, respectively, about 5 wt. % to 20 wt. % of a cycloaliphatic hydrocarbon resin, such as Escorez® 5400, about 50 wt. % to 70 wt. % of liquid tackifying hydrocarbon resin, such as Wingtack®10, and about 0 to 2 wt. % of an antioxidant, such as Irganox®1010 from Ciba Specialty Chemicals, Inc.

Each of the walls 16, 18 may be adhesively laminated to the nonwoven layer 24, 26 using the sound absorbing adhesive layer 28, 30 therebetween. The nonwoven layers 24, 26 can be formed of any suitable nonwoven materials such as a nonwoven having a basis weight of about 40 grams per square meter (gsm) of polyethylene fibers. Preferably, at least one of the non-woven layers 24, 26 is formed of a sound absorbing non-woven material. The sound absorbing non-woven material may be formed from fibers comprising a vinyl-bond rich triblock copolymer, such as a vinyl-bond rich SIS block copolymer, e.g. Hybrar® 5125 and 5127, or a vinyl-bond rich SEPS block copolymer, e.g. Hybrar® 7125.

In one embodiment, the fibers are formed of a blend of a vinyl-bond rich triblock copolymer, and polyethylene (PE) or polypropylene (PP). In another embodiment, the fibers are formed of a blend of a vinyl-bond rich SEPS block copolymer, such as Hybrar® 7125, and at least one other polymer. For example, the fibers are formed from a blend of Hybrar® 7125 and a SEPS block copolymer, such as Septon®, which is available from Kuraray Co. Ltd. The Septon® SEPS is distinguishable from Hybrar® 7125 in that the midblock of the Septon® SEPS is a hydrogenated polyisoprene whereas the midblock of Hybrar® 7125 is hydrogenated vinyl-polyisoprene. Surprisingly, test results indicate that the vinyl-bond rich Hybrar® 7125 provides significantly better sound absorbing properties than Septon® SEPS. In another example, the fibers are formed from a blend of a low molecular weight vinyl-bond rich SEPS block copolymer, such as HG664 from Kuraray Co. Ltd., a Septon® SEPS block copolymer, and a low molecular weight PP.

In some embodiments, the fibers have a sheath and core structure, in which the core is formed of Hybrar® and the sheath is formed of PE or PP. In such an embodiment, the tacky Hybrar® core is enclosed by the sheath, which is advantageous during manufacturing of non-woven materials from the fibers. The sound absorbing non-woven material can be formed by carding and dry-laying such fibers. Alternatively, the non-woven material can be formed via melt blown or spunbond technologies.

Although the ostomy pouch embodiment of FIG. 1 is provided with a nonwoven layer on both the body side and the outer side of the pouch, in other embodiments, an ostomy pouch may be provided with a nonwoven layer on only one side. For example, the body side wall (i.e. the first wall 16) can be laminated to a nonwoven layer using a sound absorbing adhesive, while the outside wall (i.e. the second wall 18) is free of a nonwoven layer or a sound absorbing adhesive layer. Alternatively, the outside wall can be laminated to a nonwoven layer by a sound absorbing adhesive, while the body side wall is free of a nonwoven layer or a sound absorbing adhesive layer.

Although the embodiment shown in FIG. 1 is a one-piece ostomy appliance with a closed-end pouch, the above discussed multilayer films, sound absorbing adhesives, and sound absorbing nonwovens can be used to make other types of ostomy appliances, such as two-piece ostomy appliances and drainable ostomy pouches.

EXAMPLES AND TEST RESULTS

Six different sample adhesive compositions comprising a vinyl-bond rich SIS block copolymer were prepared. A control sample was prepared using a pressure sensitive hot melt adhesive available under the tradename Dermatak® from Henkel. The Dermatak® adhesive comprises high molecular weight triblock and diblock copolymers, a paraffinic white oil, an end block modifying resin, and a cycloaliphatic resin (tackifier), and is typically used in skin contact applications including transdermal drug delivery applications. Dynamic Mechanical Analysis (DMA) was conducted for the samples at an oscillation frequency of 10 rad/s, during which dynamic modulus including storage modulus (G'), loss modulus (G"), and complex modulus (G*) were measured. The dynamic modulus values correlate to viscosity and rigidity of an adhesive. For example, higher the G' value, higher the viscosity and rigidity of an adhesive. Further, tangent delta (Tan Δ) values, which correlate to sound absorbing properties of an adhesive, were also measured. For example, a higher Tan Δ value correlates to a higher sound absorbing property.

Sample adhesive AL-43-73-2 was formulated with 15 parts by weight (PBW) (about 14.2 wt. %) Escorez®5400 (a cycloaliphatic hydrocarbon tackifier), 65PBW (about 61.3 wt. %) Wingtack®10 (a hydrocarbon tackifier), 15PBW (about 14.2 wt. %) Kristalex®3085 (an alpha-methyl styrene end block modifying resin), 10PBW (about 9.4 wt. %) Hybrar®5125 (a vinyl-bond rich SIS block copolymer), and 1PBW (about 0.9 wt. %) Irganox®1010 (a phenolic primary antioxidant.)

Sample adhesive AL-43-73-3 was formulated with 15PBW (about 14.2 wt. %) Escorez®5400, 65PBW (about 61.3 wt. %) Wingtack®10, 15PBW (about 14.2 wt. %) Kristalex®3085, 10PBW (about 9.4 wt. %) Hybrar®5127 (a vinyl-bond rich SIS block copolymer), and 1PBW (about 0.9 wt. %) Irganox®1010.

Sample adhesive AL-43-73-4 was formulated with 15PBW (about 12.4 wt. %) Escorez®5400, 65PBW (about 53.7 wt. %) Wingtack®10, 15PBW (about 12.4 wt. %) Kristalex®3085, 25PBW (about 20.7 wt. %) Hybrar®5125, and 1PBW (about 0.8 wt. %) Irganox®1010.

Sample adhesive AL-43-73-9 was formulated with 15PBW (about 14.2 wt. %) Escorez®5400, 65PBW (about 61.3 wt. %) Wingtack®10, 15PBW (about 14.2 wt. %) Kristalex®3085, 10PBW (about 9.4 wt. %) Hybrar®5125, and 1PBW (about 0.9 wt. %) Irganox®1010.

Sample adhesive AL-43-73-10 was formulated with 23PBW (about 21.7 wt. %) Escorez®5400, 57PBW (about 53.8 wt. %) Wingtack®10, 15PBW (about 14.2 wt. %) Kristalex®3085, 10PBW (about 9.4 wt. %) Hybrar®5125, and 1PBW (about 0.9 wt. %) Irganox®1010.

Sample adhesive AL-43-73-11 was formulated with 23PBW (about 21.7 wt. %) Escorez®5400, 57PBW (about 53.8 wt. %) Wingtack®10, 15PBW (about 14.2 wt. %) Kristalex®3085, 10PBW (about 9.4 wt. %) Hybrar®5125, and 1PBW (about 0.9 wt. %) Irganox®1010. The sample adhesive formulations are summarized in Table 1.

TABLE 1

| | Sample Adhesive Formulations | | | | | |
|---|---|---|---|---|---|---|
| Ingredients | AL-43-73-2 (wt. %) | AL-43-73-3 (wt. %) | AL-43-73-4 (wt. %) | AL-43-73-9 (wt. %) | AL-43-73-10 (wt. %) | AL-43-73-11 (wt. %) |
| Escorez ®5400 | 14.2 | 14.2 | 12.4 | 14.2 | 21.7 | 21.7 |
| Wingtack ®10 | 61.3 | 61.3 | 53.7 | 61.3 | 53.8 | 53.8 |
| Kristalex ®3085 | 14.2 | 14.2 | 12.4 | 14.2 | 14.2 | 14.2 |
| Hybrar ®5125 | 9.4 | — | 20.7 | 9.4 | 9.4 | 9.4 |
| Hybrar ®5127 | — | 9.4 | — | — | — | — |
| Irganox ®1010 | 0.9 | 0.9 | 0.8 | 0.9 | 0.9 | 0.9 |

The dynamic modulus values and tangent delta values are summarized in Table 2.

TABLE 2

| | Dynamic Modulus and Tangent Delta Values | | | | | |
|---|---|---|---|---|---|---|
| | Dynamic Mechanical Analysis at 10 rad/s | | | | | |
| | G' at 25° C. (Pa) | G" at 25° C. (Pa) | G* at 25° C. (Pa) | Tan Δ at 25° C. | Temp (tanΔ peak) (° C.) | Peak Tan Δ |
| Control | 15,942 | 5,935 | 17,013 | 0.4 | -10.5 | 4.2 |
| AL-43-73-2 | 43,160 | 321,000 | 323,900 | 7.4 | 20.4 | 8.5 |
| AL-43-73-3 | 56,020 | 306,700 | 311,800 | 5.5 | 18.5 | 7.4 |
| AL-43-73-4 | 47,170 | 74,580 | 88,250 | 1.6 | 9.0 | 5.3 |
| AL-43-73-9 | 29,890 | 156,123 | 158,943 | 5.2 | 17.9 | 8.6 |
| AL-43-73-10 | 40,919 | 248,576 | 248,307 | 6.1 | 18.0 | 8.2 |
| AL-43-73-11 | 55,430 | 320,145 | 336,835 | 5.7 | 20.4 | 7.2 |

As can be seen in Table 2, the sample adhesive formulations including a vinyl-bond rich SIS block copolymer (i.e.

Hybrar® 5125 or Hybrar® 5127) had substantially higher tangent delta values than the control adhesive sample, which were prepared from an adhesive used in some known ostomy pouches to laminate a nonwoven to a pouch wall. The higher tangent values indicate that the adhesive formulations including the vinyl-bond rich SIS block copolymer can provide significantly improved sound absorbing properties for an ostomy pouch, when compared to the same ostomy pouch made using the control adhesive. Further, although the sample adhesive formulations had higher dynamic modulus values than the control adhesive sample, physical characteristic evaluations of the sample adhesive formulations indicate that these adhesive formulations have sufficient viscosity and rigidity for laminating a nonwoven to a pouch wall.

A sample adhesive composition comprising a vinyl-bond rich SEPS block copolymer and a control adhesive sample, which is a typical adhesive formulation for bonding a nonwoven to a film layer, such as those used in disposable diaper applications, were prepared. Dynamic Mechanical Analysis (DMA) was conducted for the samples at an oscillation frequency of 10 rad/s, during which dynamic modulus including storage modulus (G'), loss modulus (G"), and complex modulus (G*), and tangent delta (Tan Δ) values were measured. Further, Tan Δ values between about 150 Hz and 2,000 Hz frequencies, which are important indication of sound absorbing properties in ostomy applications, were also measured.

Sample adhesive 42-40-3 was formulated with about 9.9 wt. % Escorez®5400 (a cycloaliphatic hydrocarbon tackifier), about 59.4 wt. % Wingtack®10 (a hydrocarbon tackifier), about 29.7 wt. % Hybrar®7311 (a vinyl-bond rich SEEPS block copolymer), and about 1 wt. % Irganox®1010 (a phenolic primary antioxidant.)

Control adhesive sample was formulated with about 59.5 wt. % Eastotac®H100W from Eastman (a tackifier based on hydrogenated hydrocarbon resin), about 20 wt. % Calsol®5550 from Calumet (a naphthenic process oil), about 20 wt. % Kraton®1165 from Kraton (a SIS block copolymer), and about 1 wt. % Irganox®1010. The sample adhesive formulation and the control adhesive formulation are summarized in Table 3.

TABLE 3

Adhesive Sample Formulations

| Ingredients | 42-40-3 (wt. %) | Control (wt. %) |
| --- | --- | --- |
| Escorez ®5400 | 9.9 | |
| Eastotac ®H100W | | 59.5 |
| Calsol ®5550 | | 20 |
| Wingtack ®10 | 59.4 | |
| Kraton ®1165 | | 20 |
| Hybrar ®7311 | 29.7 | |
| Irganox ®1010 | 1 | 0.5 |

The data from Dynamic Mechanical Analysis (DMA) at frequency of 10 rad/s are summarized in Table 4.

TABLE 4

Dynamic Mechanical Analysis Data

| | G' at 25° C. (Pa) | G" at 25° C. (Pa) | G* at 25° C. (Pa) | Tan Δ at 25° C. | Peak Tan Δ |
| --- | --- | --- | --- | --- | --- |
| Control | 1,276,061 | 2,934,472 | 3,200,417 | 2.3 | 3.4 |
| 42-40-3 | 109,600 | 71,043 | 130,613 | 0.7 | 3.6 |

Figure 3:
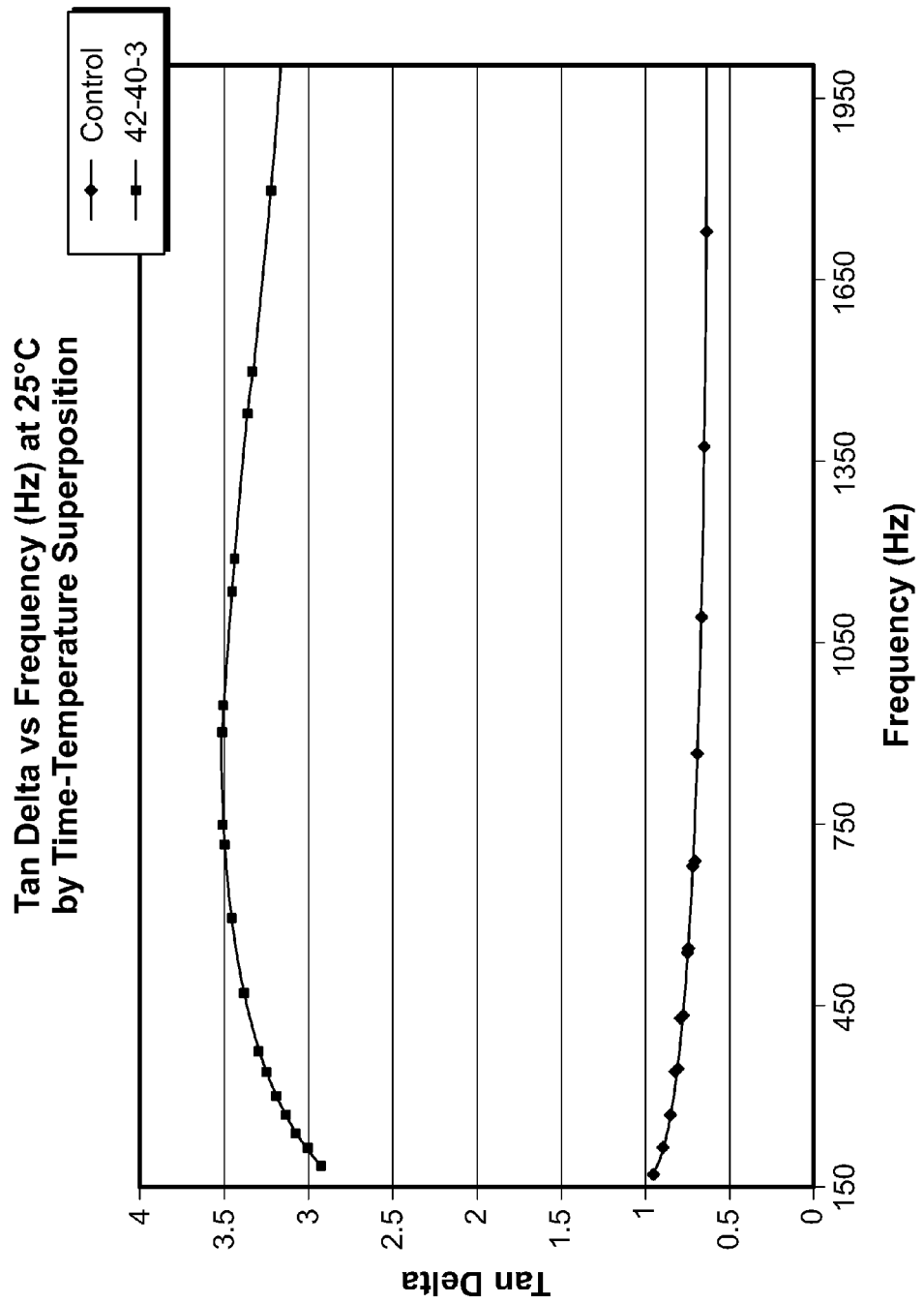
FIG. 3 is a graph showing tangent delta data for a sound absorbing adhesive sample and a control adhesive sample.

FIG. 3 is a graph showing tan Δ values between about 150 Hz and 2,000 Hz. As can be seen in FIG. 3, Sample adhesive 42-40-3 including a vinyl-bond rich SEEPS block copolymer (i.e. Hybrar® 7311) had substantially higher tangent delta values between 150 Hz and 2,000 Hz frequencies than the control adhesive sample. These higher tangent values indicate that the adhesive formulation including the vinyl-bond rich SEPS or SEEPS block copolymer can provide significantly improved sound absorbing properties for an ostomy pouch, when compared to the same ostomy pouch made using the control adhesive. Further, Sample adhesive 42-40-3 had significantly lower dynamic modulus values than the control adhesive sample, indicating that Sample adhesive 42-40-3 is a softer adhesive with a lower viscosity than the control adhesive, which is advantageous for ostomy applications.

Two asymmetric five-layer film samples (290-1 and 290-2) were prepared and tested along with a commercial ostomy pouch film sample for performance comparisons. The Sample 290-1 and Sample 290-2 were configured similar to the five-layer film 40 shown in FIG. 2.

TABLE 5

Asymmetric Five-Layer Film Samples

| Sample# | Seal | Inner | Tie | Barrier | Outer |
| --- | --- | --- | --- | --- | --- |
| 290-1 (40 μm) | (14 μm) Blend - 49 wt. % Escorene ®FL00218 + 49 wt. % Vistamaxx ®3980FL + 2 wt. % Polybatch ®SAB-1982VA) | (14 μm) Blend - 65 wt. % Vistamaxx ®3980FL + 35 wt. % Adflex ®Q100F | (4 μm) Lotader ® 4503 | (4 μm) Blend - 85 wt. % Selar ® PA3426R + 15 wt. % Lotader ® 4720 | (4 μm) Lotader ® 4503 |
| 290-2 (32 μm) | (13 μm) Blend - 49 wt. % Escorene ®FL00218 + 49 wt. % Vistamaxx ®3980FL + 2 wt. % Polybatch ® SAB-1982VA) | (9 μm) Blend - 65 wt. % Vistamaxx ®3980FL + 35 wt. % Adflex ®Q100F | (3 μm) Lotader ® 4503 | (4 μm) Blend - 85 wt. % Selar ® PA3426R + 15 wt. % Lotader ® 4720 | (3 μm) Lotader ® 4503 |

TABLE 6

Commercial Ostomy Pouch Film Sample

| Seal | Tie | Barrier | Tie | Inner | Skin |
|---|---|---|---|---|---|
| (22.5 μm) Blend - 97.5 wt. % Escorene® FL00218 + 2.5 wt. % Polybatch® SAB-1982VA) | (4 μm) Blend - 80 wt. % Lotryl® 18MA02 + 20 wt. % Bynel® CXA41E710 | (4 μm) Blend - 85 wt. % Selar® PA3426R + 15 wt. % Lotader® 4720 | (4 μm) Blend - 80 wt. % Lotryl® 18MA02 + 20 wt. % Bynel® CXA41E710 | (18 μm) Escorene® FL00218 | (4.5 μm) Blend - 98 wt. % Escorene® FL00218 + 2 wt. % Polybatch® SAS |

Sample 290-1 had a total thickness of about 40 μm and included a seal layer 42 having a thickness of about 14 μm, an inner layer 44 having a thickness of about 14 μm, a tie layer 46 having a thickness of about 4 μm, a barrier layer 48 having a thickness of about 4 μm, and an outer layer 50 having a thickness of about 4 μm. The seal layer 42 was formed from a blend including about 49 wt. % EVA (Escorene® FL00218), about 49 wt. % EP copolymer (Vistamaxx® 3980FL), and about 2 wt. % anti-block and slip additive (Polybatch® SAB-1982VA). The inner layer 44 was formed from a blend including about 65 wt. % EP copolymer (Vistamaxx® 3980FL) and about 35 wt. % PP-EP rubber (Adflex® Q100F). The tie layer 46 was formed from EMA-MAH (Lotader®4503). The barrier layer 48 was formed from a blend including about 85 wt. % amorphous polyamide (Selar® PA3426R), and about 15 wt. % E-EA-MAH (Lotader® 4720). The outer layer 50 was formed from EMA-MAH (Lotader®4503).

Sample 290-2 had a total thickness of about 32 μm and included a seal layer 42 having a thickness of about 13 μm, an inner layer 44 having a thickness of about 9 μm, a tie layer 46 having a thickness of about 3 μm, a barrier layer 48 having a thickness of about 4 μm, and an outer layer 50 having a thickness of about 3 μm. The seal layer 42 was formed from a blend including about 49 wt. % EVA (Escorene® FL00218), about 49 wt. % EP copolymer (Vistamaxx® 3980FL), and about 2 wt. % anti-block and slip additive (Polybatch® SAB-1982VA). The inner layer 44 was formed from a blend including about 65 wt. % EP copolymer (Vistamaxx® 3980FL) and about 35 wt. % PP-EP rubber (Adflex® Q100F). The tie layer 46 was formed from EMA-MAH (Lotader®4503). The barrier layer 48 was formed from a blend including about 85 wt. % amorphous polyamide (Selar® PA3426R), and about 15 wt. % E-EA-MAH (Lotader® 4720). The outer layer 50 was formed from EMA-MAH (Lotader®4503).

The commercial ostomy pouch film sample (Table 6) had a total thickness of about 57 μm and included a seal layer having a thickness of about 22.5 μm, a tie layer having a thickness of about 4 μm, a barrier layer having a thickness of about 4 μm, a tie layer having a thickness of about 4 μm, an inner layer having a thickness of about 18 μm, and a skin layer having a thickness of about 4.5 μm. The seal layer was formed from a blend including about 97.5 wt. % EVA (Escorene® FL00218) about 2.5 wt. % anti-block and slip additive (Polybatch® SAB-1982VA). The two tie layers were formed from about 80 wt. % EMA (Lotryl®18MA02) and about 20 wt. % LLDPE-MAH (Bynel®CXA41E710). The barrier layer was formed from a blend including about 85 wt. % amorphous polyamide (Selar® PA3426R), and about 15 wt. % E-EA-MAH (Lotader® 4720). The inner layer was formed from EVA (Escorene® FL00218). The skin layer was formed from a blend including about 98 wt. % EVA (Escorene® FL00218) about 2 wt. % anti-block additive (Polybatch® SAS).

The Samples were tested for Elmendorf tear, tensile strength, and modulus.

TABLE 7

Film Properties

| Film Samples | Elmendorf Tear (at 800 mm), gf/mil | | Tensile Strength (psi) | | Modulus (ksi) | |
|---|---|---|---|---|---|---|
| | MD | CD | MD | CD | MD | CD |
| Commercial Ostomy Film | 19.3 | 15.2 | 3258 | 2078 | 28.5 | 27.2 |
| Sample 290-1 | 21.4 | 20.5 | 3045 | 2552 | 38.4 | 33.9 |
| Sample 290-2 | 13.8 | 17.9 | 3698 | 2074 | 43.9 | 30.3 |

MD—Machine Direction; CD—Cross Direction

As shown in Table 7, the asymmetric film samples having a significantly smaller thickness than the commercial ostomy film sample (i.e. Sample 290-1 with about 40 μm thickness and Sample 290-2 with about 32 μm, compared to the commercial ostomy film sample with 57 μm) exhibited comparable or better film properties with regard to Elmendorf tear, tensile strength and modulus, and thus for ostomy pouches.

In the present disclosure, the words "a" or "an" are to be taken to include both the singular and the plural. Conversely, any reference to plural items shall, where appropriate, include the singular. All of the concentrations noted herein as percentage are percentage by weight unless otherwise noted.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy pouch, comprising:
a first wall;
a second wall, wherein the first wall and the second wall are sealed along their peripheral edges to define a cavity;
wherein at least one of the first wall and the second wall is formed from an asymmetric multilayer film consisting essentially of a seal layer/inner layer/tie layer/barrier layer/outer layer construction;
wherein the seal layer is formed from a blend comprising ethylene vinyl acetate copolymer (EVA) and ethylene-propylene copolymer (EP copolymer), the inner layer is formed from a blend comprising EP copolymer and polypropylene/ethylene-propylene rubber (PP-EP rubber), the tie layer is formed from a maleated ethylene methyl acrylate copolymer (EMA-MAH), the barrier layer is formed from a blend comprising an amorphous polyamide and a functionalized rubber compound, and the outer layer is formed from EMA-MAH;
wherein a combined thickness of the seal layer, the inner layer, and the tie layer is about 20 µm to about 40 µm, and a thickness of the outer layer is about 2 µm to about 10 µm, and a total thickness of the asymmetric multilayer film is about 25 µm to about 50 µm; and
wherein the asymmetric multilayer film has an Elmendorf tear strength at 800 mm of about 13.8 gf/mil to about 21.4 gf/mil, and tensile strength of about 2074 psi to about 3698 psi.

2. The ostomy pouch of claim 1, wherein the seal layer has a thickness of about 5 µm to about 30 µm, the inner layer has a thickness of about 0 µm to about 25 µm, the tie layer has a thickness of about 2 µm to about 8 µm, and the barrier layer has a thickness of about 2 µm to about 10 µm.

3. The ostomy pouch of claim 1, wherein the seal layer has a thickness of about 14 µm, the inner layer has a thickness of about 14 µm, the tie layer has a thickness of about 4 µm, the barrier layer has a thickness of about 4 µm, and the outer layer has a thickness of about 4 µm.

4. The ostomy pouch of claim 1, wherein the seal layer has a thickness of about 13 µm, the inner layer has a thickness of about 9 µm, the tie layer has a thickness of about 3 µm, the barrier layer has a thickness of about 4 µm, and the outer layer has a thickness of about 3 µm.

5. The ostomy pouch of claim 1, further comprising a nonwoven layer adhesively attached to at least one of the first and second wall, wherein an adhesive layer is arranged between the outer layer of the asymmetric multilayer film and the nonwoven layer.

6. The ostomy pouch of claim 5, wherein the adhesive layer is formed from a sound absorbing adhesive including a vinyl-bond-rich triblock copolymer.

* * * * *

UNITED STATES PATENT AND TRADEMARK OFFICE
CERTIFICATE OF CORRECTION

PATENT NO. : 9,931,239 B2  
APPLICATION NO. : 14/204474  
DATED : April 3, 2018  
INVENTOR(S) : Chang et al.

Page 1 of 1

It is certified that error appears in the above-identified patent and that said Letters Patent is hereby corrected as shown below:

On the Title Page

Column 2, Line 1, Item (56), Other Publications, delete "Goup," and insert -- Group, --, therefor.

In the Specification

Column 1, Line 38, delete "al," and insert -- al., --, therefor.
Column 4, Line 28, delete "2 ∞m" and insert -- 2 μm --, therefor.
Column 5, Line 9, delete "Arkema" and insert -- Arkema, --, therefor.
Column 8, Line 28, delete "16 wt. %)" and insert -- 16 wt. % --, therefor.
Column 12, Line 26, delete "A" and insert -- Δ --, therefor.

Signed and Sealed this
Thirteenth Day of November, 2018

Andrei Iancu
*Director of the United States Patent and Trademark Office*